(12) United States Patent
Teo et al.

(10) Patent No.: US 10,580,615 B2
(45) Date of Patent: Mar. 3, 2020

(54) SYSTEM AND METHOD FOR PERFORMING FAILURE ANALYSIS USING VIRTUAL THREE-DIMENSIONAL IMAGING

(71) Applicant: GLOBALFOUNDRIES INC., Grand Cayman (KY)

(72) Inventors: Kok Hin Teo, Schenectady, NY (US); Jay A. Mody, Clifton Park, NY (US); Jeffrey B. Riendeau, Ballston Lake, NY (US); Philip V. Kaszuba, Essex Junction, VT (US); Jian Qiu, Clifton Park, NY (US)

(73) Assignee: GLOBALFOUNDRIES INC., Grand Cayman (KY)

( * ) Notice: Subject to any disclaimer, the term of this patent is extended or adjusted under 35 U.S.C. 154(b) by 158 days.

(21) Appl. No.: 15/912,641

(22) Filed: Mar. 6, 2018

(65) Prior Publication Data
US 2019/0279840 A1 Sep. 12, 2019

(51) Int. Cl.
*H01J 37/28* (2006.01)
*G01N 21/95* (2006.01)
(Continued)

(52) U.S. Cl.
CPC .......... *H01J 37/28* (2013.01); *G01N 21/8806* (2013.01); *G01N 21/9501* (2013.01);
(Continued)

(58) Field of Classification Search
CPC ...... G06F 17/5081; G03F 7/0002; G03F 1/50; G01N 21/8806; G01N 21/9501;
(Continued)

(56) References Cited

U.S. PATENT DOCUMENTS

RE33,213 E    5/1990  Borden
5,216,481 A   6/1993  Minato
(Continued)

OTHER PUBLICATIONS

Pablo A. Vasquez Guzman, "Generating Anaglyphs from Light Field Images," Department of Mechanical Engineering, Stanford University, pp. 1-5, https://web.stanford.edu/class/ee368/Project_Autumn_1516/Reports/Guzman.pdf, Retrieved on Oct. 30, 2017.

(Continued)

*Primary Examiner* — Jingge Wu
(74) *Attorney, Agent, or Firm* — Gibb & Riley, LLC; Anthony J. Canale

(57) ABSTRACT

Disclosed are a system and method, wherein, during manufacturing of integrated circuit chips on a semiconductor wafer, an in-line optical inspection is performed to acquire a two-dimensional (2D) image of an area of the semiconductor wafer and to confirm and classify a defect in the area. The 2D image is then converted into a virtual three-dimensional (3D) image. To ensure that the 3D image is accurate, techniques are employed to determine the topography of the surface shown in the 2D image based on material-specific image intensity information and, optionally, to filter out any edge effects that result in anomalies within the 3D image. The resulting 3D image is usable for performing an in-line failure analysis to determine a root cause of a defect. Such an in-line failure analysis can be performed significantly faster than any off-line failure analysis and, thus, allows for essentially real-time advanced process control (APC).

20 Claims, 9 Drawing Sheets

(51) Int. Cl.

| | | |
|---|---|---|
| *G01N 21/88* | (2006.01) | |
| *G01R 31/265* | (2006.01) | |
| *G06T 7/521* | (2017.01) | |

(52) U.S. Cl.

CPC .......... *G01R 31/2656* (2013.01); *G06T 7/521* (2017.01); *H01J 2237/24578* (2013.01); *H01J 2237/24592* (2013.01); *H01J 2237/2814* (2013.01)

(58) Field of Classification Search

CPC ................ G01R 31/2656; G06T 19/20; G06T 2219/2004; G06T 7/521; H01J 2237/24578; H01J 2237/24592; H01J 2237/2814; H01J 37/28

See application file for complete search history.

(56) References Cited

U.S. PATENT DOCUMENTS

| | | | | |
|---|---|---|---|---|
| 6,071,315 | A * | 6/2000 | Ramamurthi | G03F 1/50 257/618 |
| 6,201,240 | B1 | 3/2001 | Dotan et al. | |
| 6,432,729 | B1 | 8/2002 | Mundt et al. | |
| 6,472,662 | B1 | 10/2002 | Archie | |
| 6,549,288 | B1 | 4/2003 | Migdal et al. | |
| 8,832,620 | B1 * | 9/2014 | Fried | G06F 17/5081 716/110 |
| 2004/0252879 | A1 * | 12/2004 | Tiemeyer | G01N 21/9501 382/145 |
| 2005/0004774 | A1 * | 1/2005 | Volk | G01N 21/9501 702/108 |
| 2005/0031186 | A1 | 2/2005 | Luu et al. | |
| 2006/0001877 | A1 * | 1/2006 | Moriya | G01N 21/47 356/369 |
| 2006/0278826 | A1 * | 12/2006 | Roberts | H01J 37/222 250/310 |
| 2006/0281200 | A1 * | 12/2006 | Cadouri | G06F 17/5068 438/14 |
| 2011/0216312 | A1 * | 9/2011 | Matsumoto | G01N 21/9501 356/237.1 |
| 2011/0265048 | A1 * | 10/2011 | Kim | G06F 17/5081 716/53 |
| 2012/0316855 | A1 * | 12/2012 | Park | G01N 21/9501 703/13 |
| 2013/0215420 | A1 * | 8/2013 | Liu | G01N 21/9501 356/237.5 |
| 2014/0278266 | A1 * | 9/2014 | Faken | G06F 17/5009 703/1 |
| 2014/0282302 | A1 * | 9/2014 | Greiner | G06F 17/5045 716/54 |
| 2014/0282324 | A1 * | 9/2014 | Greiner | G06F 17/5068 716/111 |
| 2015/0007121 | A1 * | 1/2015 | Lin | G06F 17/5081 716/112 |
| 2015/0111386 | A1 * | 4/2015 | Rathsack | G03F 7/42 438/703 |
| 2016/0109376 | A1 * | 4/2016 | Pavani | G01N 21/8806 356/237.5 |
| 2016/0123897 | A1 * | 5/2016 | Pavani | G01N 21/9501 348/126 |
| 2016/0217233 | A1 * | 7/2016 | Kamon | G06F 17/5068 |
| 2018/0365370 | A1 * | 12/2018 | Egan | G06F 17/5081 |
| 2019/0286780 | A1 * | 9/2019 | Greiner | G06F 17/5068 |
| 2019/0287237 | A1 * | 9/2019 | de Bonfim Gripp | G06T 7/64 |

OTHER PUBLICATIONS

Klette et al., "Computer Vision: Three-Dimensional Data from Images," Springer-Verlag Singapore Pte. Ltd., Singapore, 1998, pp. 347-375.

Saravanan et al., "Color Image to Grayscale Image Conversion," IEEE Second International Conference on Computer Engineering Applications, 2010, pp. 196-199.

Stokowski et al., "Wafer Inspection Technology Challenges for ULSI Manufacturing," KLA-Tencor, pp. 1-11.

\* cited by examiner

SYSTEM AND METHOD FOR PERFORMING FAILURE ANALYSIS USING VIRTUAL THREE-DIMENSIONAL IMAGING

BACKGROUND

Field of the Invention

The present invention relates to failure analysis and, more specifically, to a system and method that use virtual three-dimensional (3D) imaging to perform an in-line failure analysis following defect detection during semiconductor wafer inspection.

Description of Related Art

In-line optical inspection tools, such as scanning electron microscopes (SEM), are often employed during integrated circuit chip manufacturing (i.e., in-line). Such tools are capable of capturing a two-dimensional (2D) optical image of an area of interest on a semiconductor wafer and of using the 2D image for defect analysis and classification. If the optical inspection tool indicates that a defect may have occurred in an area of interest on a semiconductor wafer and that the defect at issue is critical, an off-line failure analysis can be performed in order to confirm and determine the root cause(s) of the defect. The off-line failure analysis typically includes a non-destructive analysis (e.g., atomic force microscopy (AFM)) and/or a destructive physical analysis (DPA) of the area of the semiconductor wafer. Based on the results of the off-line failure analysis, advanced process control (APC) can be performed (e.g., corrective actions can be taken in order to prevent the defect(s) from occurring during subsequent IC chip manufacturing). Unfortunately, the conventional off-line failure analysis can be time-consuming and unduly costly because the techniques used require sample preparation, the performance of step-by-step processes, etc. Additionally, the impact on current IC chip manufacturing can be significant (e.g., if manufacturing is halted for an extended period of time pending the results of a failure analysis or if defective IC chips continue to be manufactured while the failure analysis is being conducted).

SUMMARY

In view of the foregoing, disclosed herein are embodiments of a system, method and computer program product that employ virtual three-dimensional (3D) imaging to perform an in-line failure analysis following defect detection during semiconductor wafer inspection. Such an in-line failure analysis can be performed significantly faster and at a reduced cost than any off-line failure analysis. Thus, the disclosed embodiments allow for essentially real-time advanced process control (APC) at a relatively low cost.

More particularly, disclosed herein are embodiments of a system that includes at least a memory and an image processor. The memory can store material-specific image intensity information. The image processor can receive a two-dimensional (2D) image of a surface of an area of a semiconductor wafer (or a fragment thereof) from an optical inspection tool (e.g., a scanning electron microscope (SEM)). The 2D image can specifically be generated during an inspection performed by the optical inspection tool during manufacture of integrated circuit chips on the semiconductor wafer. The image processor can further access the material-specific image intensity information from the memory and can convert the 2D image into a virtual three-dimensional (3D) image using the material-specific image intensity information.

Specifically, the image processor can determine the image intensities of different shapes in the 2D image and can also determine the different materials of the different shapes (e.g., using a design layout stored in memory and/or using a materials analysis tool). The image processor can then retrieve, from the memory, image intensity information for each of the different materials and, based on the retrieved information, can determine the topography of the surface. Given the topography of the surface, the image processor can convert the 2D image into a virtual 3D image. Optionally, if the virtual 3D image includes an anomaly caused by an edge effect, the image processor can apply a filter to compensate for the edge effect and the virtual 3D image can be reconstructed without the anomaly. In any case, the resulting virtual 3D image can be used to perform an in-line failure analysis (i.e., to confirm the presence of a defect in the area at issue and to determine a root cause of the defect).

Also disclosed herein are embodiments of a method implemented using the above-described system. The method can include receiving, by an image processor from an optical inspection tool (e.g., a scanning electron microscope (SEM)), a two-dimensional (2D) image of a surface of an area of a semiconductor wafer (or a fragment thereof), wherein the 2D image was generated during an inspection performed by the optical inspection tool during manufacture of integrated circuit chips on the semiconductor wafer. The method can further include accessing, by the image processor, material-specific image intensity information that is stored in a memory. The method can further include converting, by the image processor, the 2D image into a virtual three-dimensional (3D) image using the material-specific image intensity information.

Specifically, the method can include determining, by the image processor, the image intensities of different shapes in the 2D image and the different materials of the different shapes. The different materials of the different shapes can, for example, be determined using a design layout stored in memory and/or a materials analysis tool. In any case, the method can further include retrieving, by the image processor from the memory, image intensity information for each of the different materials and, based on this retrieved information, determining the topography of the surface. The method can further include converting the 2D image into a virtual 3D image given the topography of the surface. Optionally, the method can also include determining, by the image processor, whether the virtual 3D image includes an anomaly caused by an edge effect and, if so, applying a filter to compensate for the edge effect and reconstructing the virtual 3D image without the anomaly. In any case, the resulting virtual three-dimensional image can be used to confirm a previously detected defect in the area at issue and for performing an in-line failure analysis to determine a root cause of the defect.

Also disclosed herein are embodiments of a computer program product. The computer program product can include a computer readable storage medium having program instructions embodied therewith. The program instructions can be executable by a computer to cause the computer to perform the above-described method.

BRIEF DESCRIPTION OF THE SEVERAL VIEWS OF THE DRAWINGS

The present invention will be better understood from the following detailed description with reference to the drawings, which are not necessarily drawn to scale and in which.

DETAILED DESCRIPTION

As mentioned above, conventional off-line failure analyses can be time-consuming and unduly costly because the techniques used require sample preparation, the performance of step-by-step processes, etc. Additionally, the impact on current IC chip manufacturing can be significant (e.g., if manufacturing is halted for an extended period of time pending the results of a failure analysis or if defective IC chips continue to be manufactured while the failure analysis is being conducted).

In view of the foregoing, disclosed herein are embodiments of a system, method and computer program product that use virtual three-dimensional (3D) imaging to perform an in-line failure analysis following defect detection during semiconductor wafer inspection. Specifically, in the embodiments, during manufacturing of integrated circuit chips on a semiconductor wafer, an inspection of the semiconductor wafer can be performed using an optical inspection tool (e.g., an scanning electron microscope (SEM) image), which generates a two-dimensional (2D) image of an area of the semiconductor wafer. The 2D image can then be converted into a virtual 3D image. However, in order to ensure that the virtual 3D image is accurate, techniques can be employed to determine the topography of the surface shown in the 2D image based on material-specific image intensity information and, optionally, to filter out any edge effects that result in anomalies within the virtual 3D image. The resulting 3D image can be used for confirming a defect, which was previously detected in the area of interest, and for performing an in-line failure analysis to determine a root cause of the defect. Such an in-line failure analysis can be performed significantly faster and at a reduced cost than any off-line failure analysis. Thus, the disclosed embodiments allow for essentially real-time advanced process control (APC) at a relatively low cost.

Figure 1:
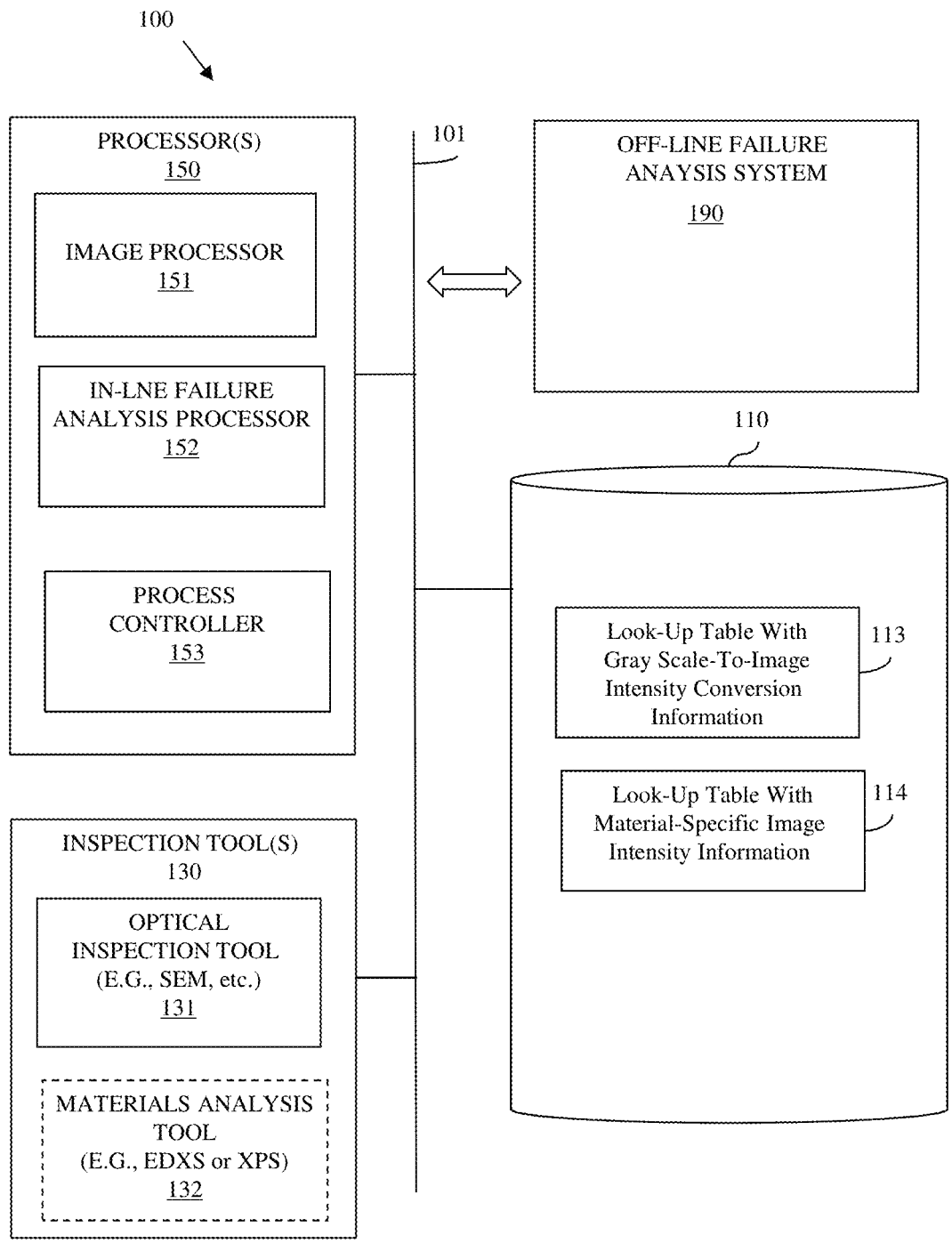
FIG. 1 is a schematic diagram illustrating an in-line failure analysis system.

More particularly, referring to FIG. 1, disclosed herein are embodiments of a system 100 that includes multiple components including, but not limited to, at least one memory 110, one or more inspection tools 130 (e.g., an optical inspection tool 131 and a materials analysis tool 132), and one or more processors 150 (e.g., an image processor 151, an in-line failure analysis processor 152, and a process controller 153). The system components (e.g., the memory, the inspection tool(s), and the processor(s)) can be interconnected (i.e., in communication) over a wire network (e.g., see the system bus 101) and/or over a wireless network.

The optical inspection tool 131 can be a device that can microscopically inspect an area of interest of a semiconductor wafer or fragment thereof during manufacturing of integrated circuit chips thereon, that can generate a digital 2D image of the area, and that can use the digital 2D image for defect analysis and classification. For example, during a preliminary inspection of defined areas of interest on semiconductor wafers, potential defects can be detected, based on threshold settings (e.g., critical dimensions, etc.). Subsequently, an in-line optical inspection of a semiconductor wafer with an area of interest having a detected defect can be performed using the optical inspection tool 131. That is, the optical inspection tool 131 can capture a digital 2D image of a surface of the area of interest and can analyze that 2D image to confirm and classify the defect. If/when a defect is confirmed and classified, for example, as a critical defect (e.g., a defect that can significantly impact yield), then the optical inspection tool 131 can forward the digital 2D image to the image processor 151 for further image processing.

The optical inspection tool 131 can be, for example, a scanning electron microscope (SEM), a transmission electron microscope (TEM) or any other suitable microscope capable of capturing a 2D image of a surface, as described. For purposes of illustration, the system is described in greater detail below with respect to a SEM. Those skilled in the art will recognize that a SEM can include, but is not limited to, the following components: a scanner that scans the surface with a beam of electrons in a raster scan pattern; an electron detector that detects secondary electrons emitted by atoms at the surface as they are excited by the electron beam; an image generator that generates a 2D SEM image of the surface based on the detected secondary electrons; and an image analyzer that analyzes the 2D SEM image in order to confirm the existence of the defect and to classify the defect by type. If/when a defect is confirmed and classified as a critical defect (e.g., a defect that can significantly impact yield), then the SEM can forward the 2D SEM image to the image processor 151 for further processing.

In any case, the image processor 151 can receive the digital 2D image from the optical inspection tool 131 and can convert that digital 2D image into a virtual three-dimensional (3D) image.

To accomplish this, the image processor 151 can begin by determining if the digital 2D image is a digital colored 2D image or a digital grayscale 2D image. If the digital 2D image is a digital colored 2D image, the image processor 151 can convert it into a digital grayscale 2D image. Techniques for converting a digital colored image into a digital grayscale image are well known in the art. Thus, the details of those techniques have been omitted from this specification in order to allow the reader to focus on the salient aspects of the disclosed system.

Next, the image processor 151 can define the materials and the topography of the surface, which is shown in the digital grayscale 2D image.

Specifically, within a grayscale 2D image and, particularly, a grayscale 2D SEM image or the like, different shapes (i.e., different features that are defined by groups of pixels) will have different image intensities. For purposes of this disclosure, "image intensity" in grayscale refers to the value assigned to a given lightness (apparent brightness) from black (e.g., at 0) to white (e.g., at 100) across the grayscale. So an image intensity that is relatively low in value will be dark (i.e., less bright) and an image intensity that is relatively high in value will correspond to light (i.e., more bright). Variations in the image intensities within the grayscale 2D image will depend upon both the different surface materials (i.e., the materials that emit the secondary electrons captured by the electron detector) and the distances between those surface materials and the electron detector.

Figure 2A:
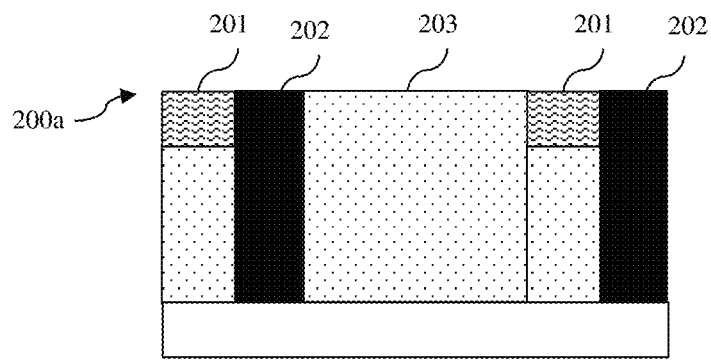
FIGS. 2A and 2B are cross-section diagrams showing different semiconductor wafer topographies.
Figure 2B:
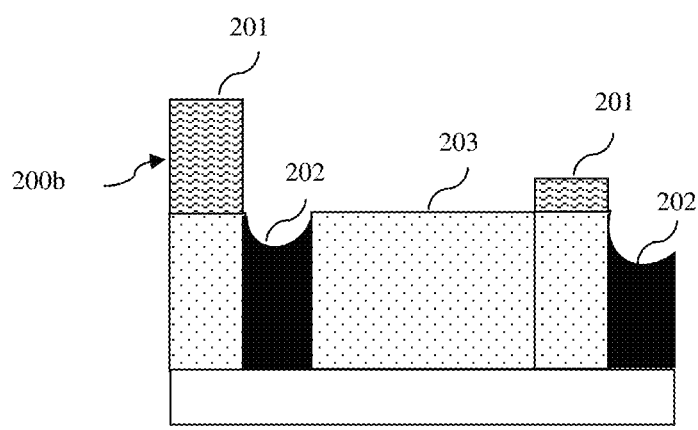

Consider the vertical cross-sections of FIGS. 2A and 2B showing different semiconductor wafer topographies. The same materials (e.g., copper 201, tungsten 202 and silicon dioxide 203) are exposed at the top surfaces 200a and 200b of the semiconductor wafers in both FIG. 2A and FIG. 2B. Since the surface 200a of FIG. 2A is level (i.e., has a flat topography), a 2D SEM image of the surface 200a would show shapes made of the same material having the same image intensity and shapes made of different materials having different image intensities. However, since the surface 200b of FIG. 2B is not level (i.e., has an uneven topography), a 2D SEM image of the surface 200b will not be the same as that of the top surface 200a and, more specifically, will show shapes of the same material at different levels with different image intensities and may further show shapes of different materials at the same or different levels with different image intensities. As a result, one could not simply look at a 2D SEM image to determine whether the different image intensities of different shapes are the result of different materials and a flat topography or whether they are the result of different materials and/or an uneven topography and, thus, could not simply look at a 2D SEM image to determine the root cause of a defect. Consequently, the system 100 must be able to define the materials exposed at the surface shown in a grayscale 2D image and also the topography of that surface before being able to convert it into a virtual 3D image.

Figure 3:
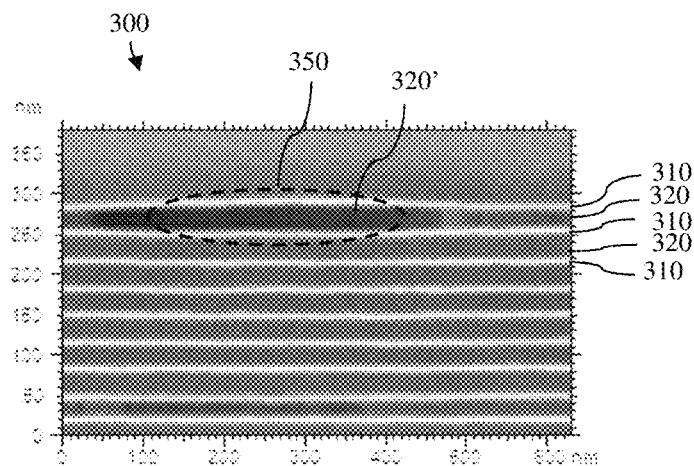
FIG. 3 is an exemplary 2D image taken by an optical inspection tool.

FIG. 3 is an exemplary 2D SEM image 300 that can be forwarded from an optical inspection tool 131 (e.g., a SEM) to the image processor 151. FIG. 3 shows the surface of an area of a semiconductor wafer. Visible at the surface are alternating light and dark stripes. The light stripes correspond to the tops of semiconductor fins 310 and the dark stripes correspond to the tops of isolation regions between the semiconductor fins 310. The image intensity of the semiconductor fins 310 is relatively high and is greater than the image intensity of the isolation regions 320, as indicated by the fact that the semiconductor fins 310 are light and the isolation regions 320 are dark. Ideally, the semiconductor fins 310 will have essentially identical widths and heights, will be essentially vertical (i.e., oriented essentially perpendicular to the substrate) and will have an essentially uniform pitch such that the spacing between each pair of adjacent semiconductor fins 310 is essentially identical. Also, ideally, the spaces between each pair of adjacent semiconductor fins 310 will be partially filled with dielectric fill material, thereby forming the isolation regions and the tops of the isolation regions will all be essentially level and below the tops of the semiconductor fins. However, FIG. 3 further shows a defect 350 within the area, where the distance between a pair of adjacent semiconductor fins is greater than some threshold distance and where the image intensity of the portion 320' of an isolation region between the adjacent semiconductor fins is lower than the image intensity of the isolation regions elsewhere in the area, as indicated by the fact that this portion 320' is darker than any other isolation region within the region. Due to the nature of the 2D image, as discussed above, one could look at the 2D SEM image shown in FIG. 3 and identify the defect 350, but could not determine either of the following: (a) whether the pair of adjacent semiconductor fins are vertical, but spaced to far apart, or whether one of the semiconductor fins is bent; and (b) whether the portion 320' of the isolation region is darker because it is made of a different material than the isolation regions elsewhere in the are or because its top surface is lower.

To determine the surface materials shown in the 2D image, the materials analysis tool 132 can perform a materials analysis of the same surface of the semiconductor wafer and can further generate a report identifying the different surface materials. For example, this material analysis tool 132 can be an energy-dispersive X-ray image spectroscope (EDXS) (also referred to in the art as an energy-dispersive X-ray analyzer or an energy-dispersive X-ray micro-analyzer). Those skilled in the art will recognize that an EDXS operates by focusing a high-energy beam (e.g., a beam, for example, of electrons or x-rays) onto the surface. The number and energy of the X-rays emitted back from the surface can be measured by an energy-dispersive spectrometer. The energies of the emitted X-rays will depend upon the atomic structure of the emitting element and, thus, the EDXS allows the material composition of different shapes depicted in the 2D image to be measured. Alternatively, the materials analysis tool 132 could be an X-ray photoelectron spectroscope (XPS) or any other suitable materials analysis tool.

Referring again to FIG. 3, the results of the materials analysis output by the materials analysis tool 132 could indicate that the light stripes are composed of a specific semiconductor material (e.g., silicon) and the dark stripes are composed of a specific dielectric material (e.g., silicon dioxide. These results can further indicate that even though the portion 320' is darker (i.e., has a lower image intensity), it is composed of the same specific dielectric material as the isolation regions elsewhere in the area. Thus, these results indicate that the topography is uneven and, particularly, that the portion 320' is farther from the electron detector.

The image processor 151 can receive the results of the materials analysis from the materials analysis tool 132 and, based on the results, can determine the topography of the surface shown in the 2D image. Specifically, the memory 110 can store grayscale to image intensity conversion information and also material-specific image intensity information that can be used to determine the topography of the surface shown in the 2D image.

For example, the memory 110 can store multiple look-up tables (LUTs) including, but not limited to, a grayscale LUT 113 and a material-specific image intensity LUT 114. The grayscale LUT 113 can include, for example, digital images from black to white on the grayscale and, for each digital image, an indication of the corresponding image intensity (e.g., from 0 to 100). The material-specific image intensity look-up table (LUT) 114 can list multiple different materials, which are used in integrated circuit (IC) chip manufacturing. These materials can include, for example, semiconductor materials (e.g., silicon, silicon germanium, silicon germanium carbide, polysilicon, etc.), dielectric materials (e.g., silicon dioxide, silicon nitride, silicon oxycarbide, etc.), metals, metal alloys, and any other material used in IC chip manufacturing. The material-specific image intensity LUT 114 can further associate specific image intensity information with each of the listed materials (i.e., can include material-specific image intensity information). The image intensity information can include, for example, the expected image intensity value of each material at a minimum distance ($d_{min}$) from the electron detector and also the expected image intensity values of each material at additional incrementally increasing distances from the electron detector (e.g., at $d_{min}$+x, at $d_{min}$+2x, at $d_{min}$+3x, and so on). It should be noted that this material-specific image intensity information can be empirically determined and can be specific for the given optical inspection tool being used.

For all the different shapes in the 2D image, the image processor 151 can access the grayscale LUT 113 and can determine the image intensity of a specific shape based on the level of brightness in the grayscale where that specific shape falls. For each specific shape in the 2D image, the image processor 151 can also access the material-specific image intensity LUT 114 and can retrieve material-specific image intensity information. Given the previously determined image intensities of the shapes in the 2D image and the previously determined surface materials of the different shapes, the image processor 151 can determine the distances (e.g., $d_{min}$, $d_{min}$+x, at $d_{min}$+2x, at $d_{min}$+3x, etc.) between those shapes and the electron detector during image capture. The image processor 151 can subsequently piece those distances together to determine the topography of the surface shown in the 2D image. It should be understood that the tops of shapes at distance $d_{min}$ will be at the highest level ($h_{max}$) of the topography, the tops of shapes at distance $d_{min}$+x will be at the second highest level ($h_{max}$−x), the tops of shapes at distance $d_{min}$+2x will be at the third highest level ($h_{max}$−2x), and so on.

Figure 4:
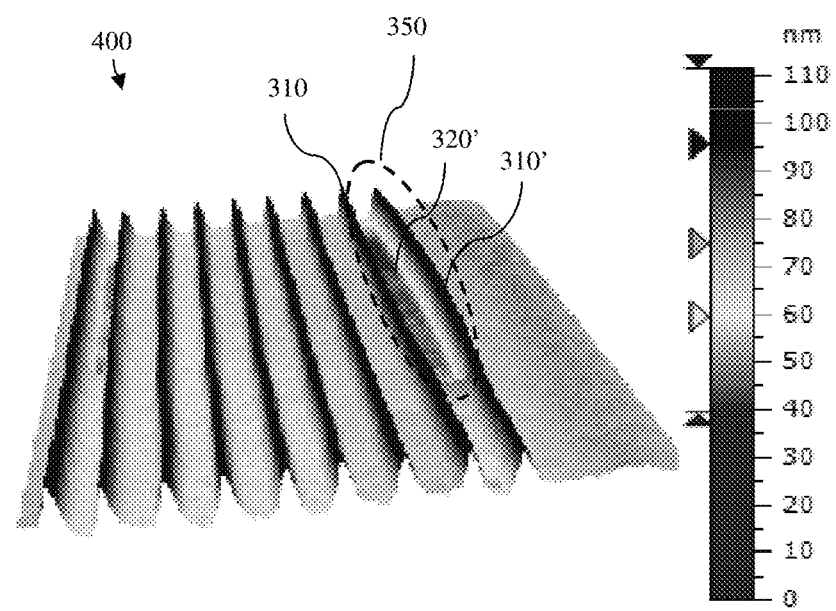
FIG. 4 is an exemplary virtual 3D image generated by the system of FIG. 1 based on the 2D image of FIG. 3.

Given the surface materials of the shapes and the topography of the surface, the image processor 151 can convert the 2D image of the area of interest on the semiconductor wafer into a virtual 3D image. To generate this virtual 3D image, the image processor 151 can use a programming language (e.g., MATLAB, Python, C++, Scilab, Mathematica, Labscript or any other suitable programming language). FIG. 4 is an exemplary virtual 3D image 400 generated, as described above, based on the 2D SEM image 300 shown in FIG. 3.

Figure 5:
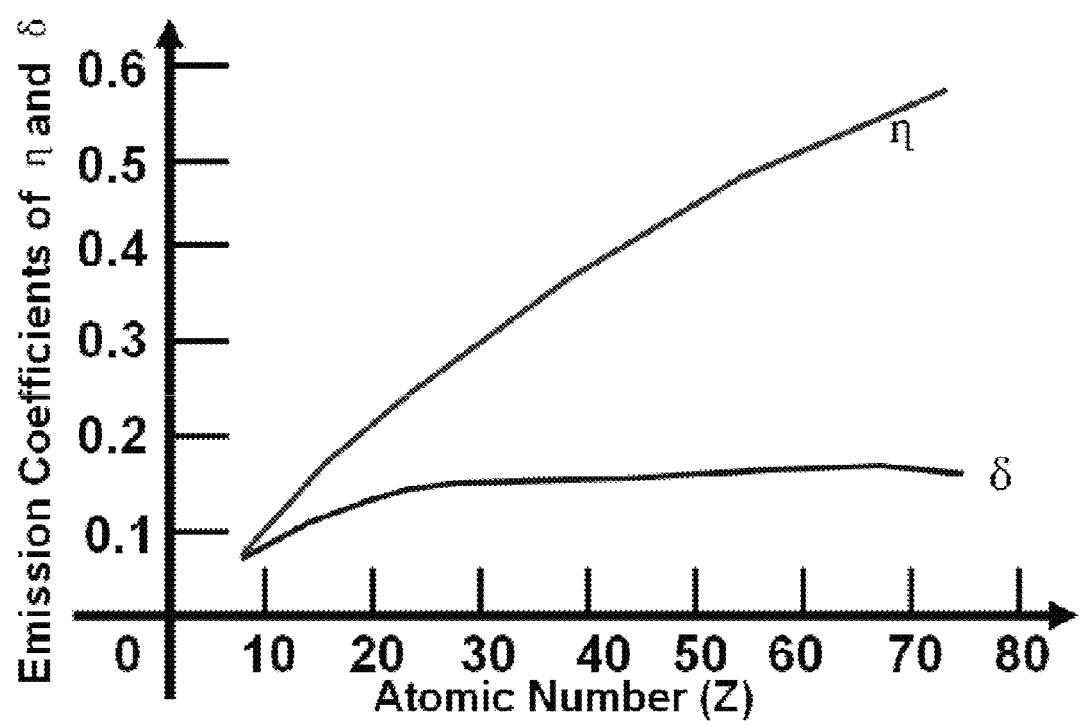
FIG. 5 is a graph illustrating a relationship between grayscale image value and contrast.

Techniques for converting 2D images into 3D images using such programming languages are well known in the art. For example, in one exemplary embodiment, the acquired 2D image from the optical inspection tool 131 (e.g., the SEM) can be in the form of a red-green-blue (RGB) image (also referred to in the art as a tricolor image). To convert such a 2D RGB image into a virtual 3D image, the 2D RGB image must first be converted into a grayscale image. However, those skilled in the art will recognize that the converted grayscale image may lose contrast, sharpness, shadow, and structure. Therefore, in order preserve contrast, sharpness, shadow, and structure of the 2D RGB image, a color-to-grayscale conversion algorithm can be used (e.g., see the color image to grayscale conversion algorithm disclosed in C. Saravanan, "Color Image to Grayscale Image Conversion," 2010 Second International Conference on Computer Engineering and Applications, Bali Island, 2010, pp. 196-199). Specifically, the luminance and chrominance values of the 2D image can be calculated and the sum of the chrominance values can be determined. Then, the RGB values can be approximated using RGB components. After that, the grayscale values can be calculated based on the average of four values of RGB and the sum of chrominance values. The RGB values of the source image (from 0 to 255) were reduced to the value range from 0 to 85. This reduction in values enhances the color range and helps to calculate the grayscale image. The grayscale value of the 2D image can then be estimated as the depth. The brighter area is close to the surface, and the darker area is far to the surface. Thus, providing us with an initial virtual 3D image. There still, however, might be an over or under-estimation of height/topography in the image. In this case, utilize SEM/EDX/XPS can be used to estimate the material differences in an image or backscattered electron image. After taking into account the material difference, the previously obtained grayscale image can be normalized to material having the highest or lowest atomic number. Specifically, the lowest value of grayscale image equals the lowest contrast (due to the backscattered electron/secondary electron yield of the EDX image) and the highest value of grayscale image equals the highest contrast of the grayscale image (due to the backscattered electron/secondary electron yield) as shown in the graph of FIG. 5.

The in-line failure analysis processor 152 can subsequently use this virtual 3D image to perform an in-line failure analysis in order to confirm the presence of the defect in the area at issue and to determine the root cause of the defect. For example, the in-line failure analysis processor 152 can evaluate the defect 350 shown in the virtual 3D image 400 of FIG. 4 and can determine that the outermost semiconductor fin 310' is tilted (i.e., bent). Furthermore, as a result of the tilted semiconductor fin 310', the space between this outermost semiconductor fin 310' and the adjacent semiconductor fin 310 is relatively wide so that the portion 320' of the isolation region between those fins only partially fills the space (i.e., the portion 320' is recessed as compared to the isolation regions elsewhere in the area).

The process controller 153 can then perform advanced process control (APC) based on the results of the in-line failure analysis. That is, the process controller 153 can cause one or more manufacturing processes to be adjusted in order to prevent re-occurrence of the defect during subsequent integrated circuit chip manufacturing (i.e., on upcoming semiconductor wafers in the manufacturing line). For example, given the root cause of the defect shown in FIG. 4, the in-line failure analysis processor 152 can adjust the processes performed during semiconductor fin formation to prevent semiconductor fin bending. Those skilled in the art would recognize that various different processes could be adjusted alone and/or in combination to prevent such semiconductor fin bending. In one embodiment, the etch specifications used during semiconductor fin formation could be adjusted to ensure that the resulting semiconductor fins are slightly tapered (e.g., slightly wider at the bottom than at the top) and, thereby more robust.

Figure 6:
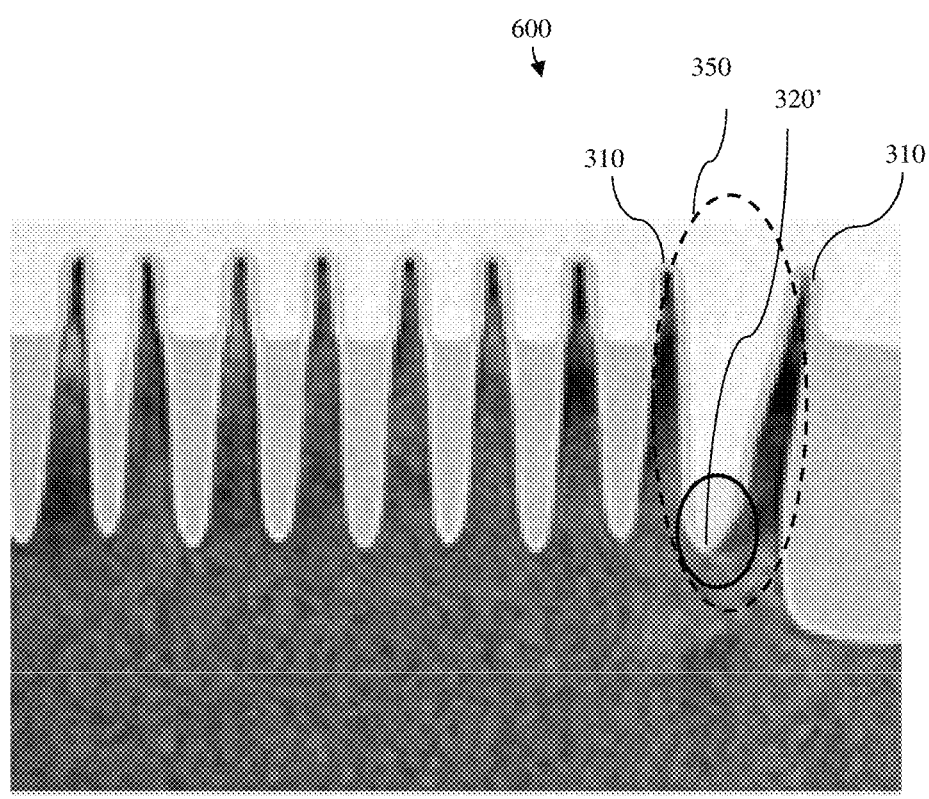
FIG. 6 is an exemplary vertical cross-section image captured during an off-line failure analysis and showing the defect.

Optionally, the system 100 can further include an off-line failure analysis system 190. Specifically, if during the in-line optical inspection, the optical inspection tool 131 confirms the existence of the defect and classifies that defect as, for example, a critical defect, the 2D image can be converted to a virtual 3D image and used for in-line failure analysis and APC, as discussed above. Optionally, the semiconductor wafer can also be sent to an off-line failure analysis system 190 in order to confirm and possible expand upon the results of the in-line failure analysis. The off-line failure analysis system 190 can perform, for example, a non-destructive analysis, such as atomic force microscopy (AFM), and/or a destructive physical analysis (DPA). FIG. 6 is an exemplary vertical cross-section image 600 captured during an off-line failure analysis and showing the defect 350. This cross-section image 600 confirms that the outermost semiconductor fin 310' is tilted (i.e., bent) and that the portion 320' of the isolation region only partially fills the space between the pair of adjacent semiconductor fins (i.e., the portion 320' is recessed as compared to the isolation regions elsewhere in the area). The off-line failure analysis system 190 can further be in communication with the processor controller 153, which can perform additional APC, as necessary, based on the results of the off-line failure analysis.

Figure 7:
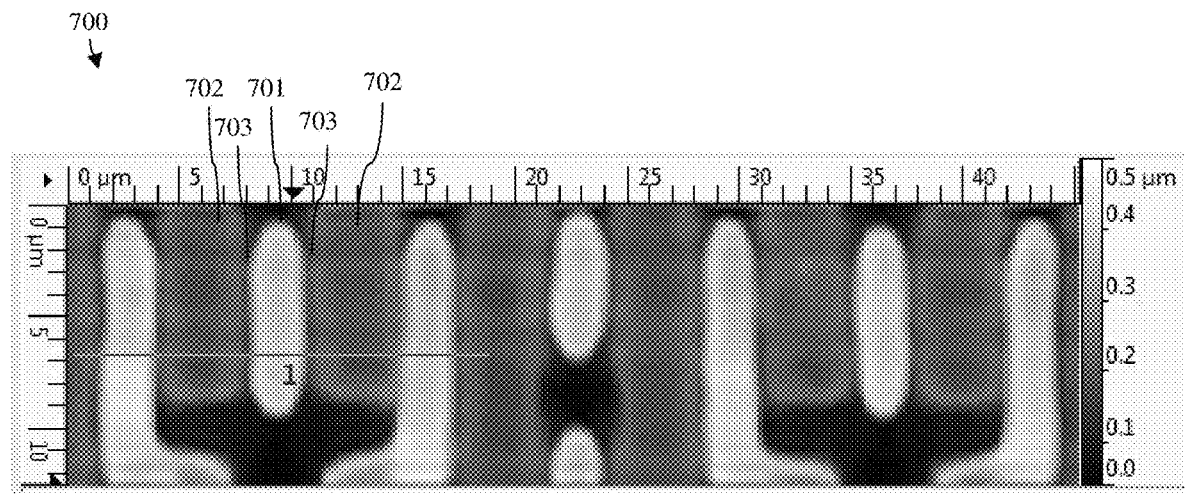
FIG. 7 is another exemplary 2D image.
Figure 8:
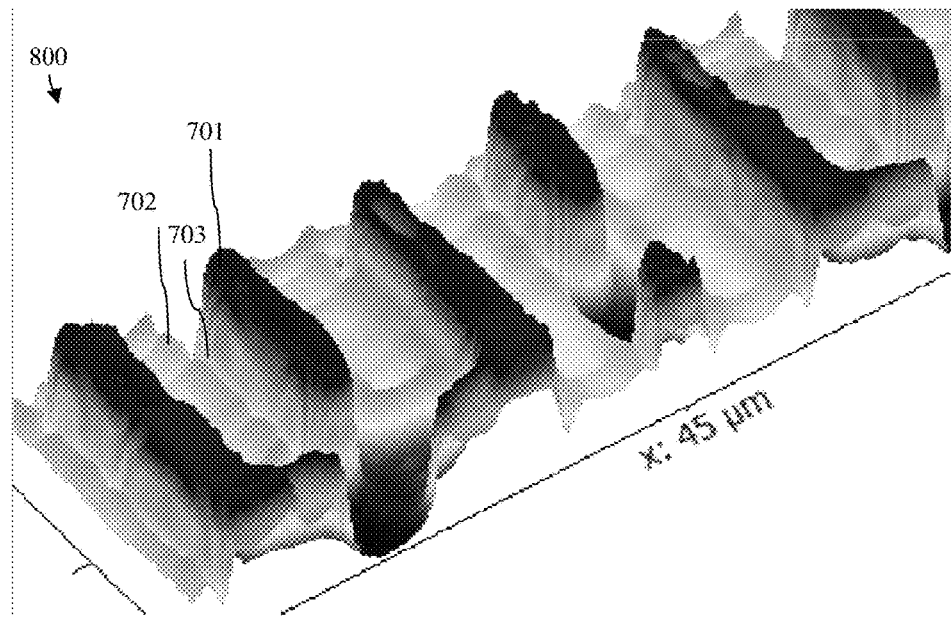
FIG. 8 shows an exemplary virtual 3D image generated by the system of FIG. 1 based on the 2D image of FIG. 6.

It should be noted that the above-described techniques, which are used by the image processor 151 to convert a 2D image into a virtual 3D image can, at times, produce edge effect-induced anomalies in the virtual 3D image. Specifically, a 2D SEM image may show lines, which correspond to the interfaces between two different materials and which have image intensities that are actually different from the immediately adjacent materials on either side. Depending upon the image intensities of these lines, they can appear as divots or bumps in the virtual 3D image. For example, FIG. 7 shows an exemplary 2D image 700 with first material shapes 701 with a high image intensity (white) positioned laterally between second material shapes 702 with a lower image intensity (gray). At the interface between the shapes 701-702 there are lines 703 with an even lower image intensity (black). FIG. 8 shows an exemplary virtual 3D image 800 generated based on the 2D image 700. In this virtual 3D image 800, the lines 703 from FIG. 8 appear as divots between the first material shapes 701 and the second material shapes 702 even though no such divots exist on the actual semiconductor wafer. Divots or bumps that do not exist but appear in the virtual 3D image because of image intensity variations at the interface between shapes of different materials in the 2D image are referred to herein as edge effect-induced anomalies.

Figure 9:
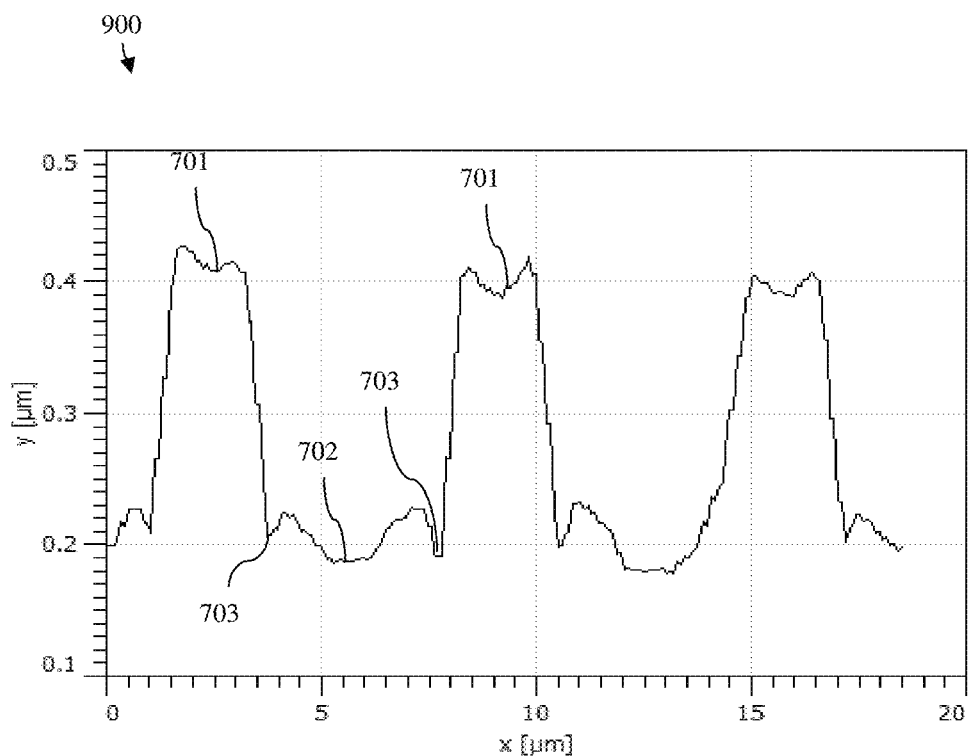
FIG. 9 is a graph illustrating the profile of the virtual 3D image of FIG. 7.
Figure 10:
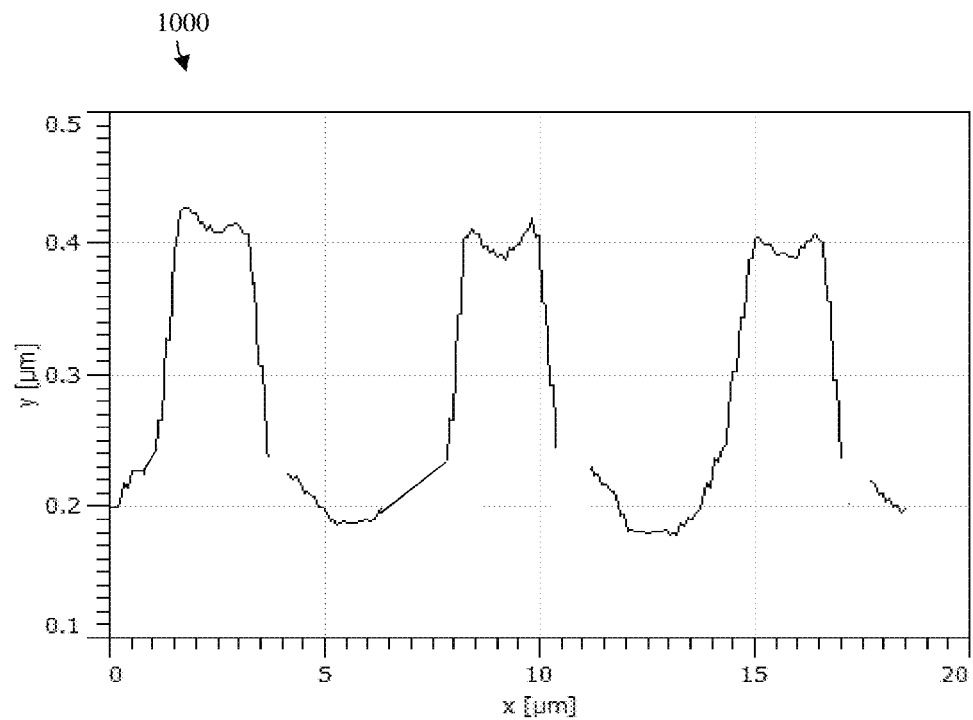
FIG. 10 is a graph illustrating a corrected profile for the virtual 3D.

Therefore, optionally, before the virtual 3D image is sent to the in-line failure analysis processor 152, the image processor 151 can further evaluate the virtual 3D image to determine whether it includes any edge effect-induced anomalies and, particularly, any divots or bumps caused by an edge effect. If so, the image processor 151 can use a filter to compensate for the edge effect and, after using of the filter, can reconstruct the virtual 3D image without the anomalies. For example, FIG. 9 is a graph 900 illustrating the profile of the virtual 3D image 800 shown in FIG. 8, including divots that correspond to the interface lines 703 from FIG. 7. FIG. 10 is a graph 1000 illustrating a corrected profile following application of the filter and reconstruction of the virtual 3D image without the divots. The image processor 151 can then forward the reconstructed virtual 3D image to the in-line failure analysis processor 152 and, for improved accuracy, the in-line failure analysis processor 152 can use this reconstructed virtual 3D image to perform the in-line failure analysis (i.e., to confirm the presence of the defect in the area at issue and to determine the root cause of the defect).

Figure 11:
FIG. 11 is a flow diagram illustrating an in-line failure analysis method.

More particularly, referring to FIG. 11, also disclosed herein are embodiments of an inspection and failure analysis method implemented using the above-described system 100 illustrated in FIG. 1.

The method can include initiating manufacturing of integrated circuit (IC) chips on semiconductor wafers (see process 1102). During manufacturing, preliminary inspection of defined areas of interest on the semiconductor wafers can be performed (e.g., after each process step is performed or after multiple process steps are performed) in order to detect potential defects, based on threshold settings (e.g., critical dimensions, etc.) (see process 1104).

An in-line optical inspection can then be performed on a semiconductor wafer with an area of interest having a detected defect (see process 1106). Specifically, this in-line optical inspection can be performed using an optical inspection tool 131 (e.g., a scanning electron microscope (SEM), a transmission electron microscope (TEM), or any other suitable optical inspection tool) to capture a two-dimensional (2D) image of a surface of the area of interest. Additionally, the 2D image can be analyzed at process 1106 to confirm and classify the defect.

If/when a defect is confirmed and classified, for example, as a critical defect (e.g., a defect that can significantly impact yield), then the digital 2D image can be further processed using an image processor 151 to convert the 2D image into a virtual 3D image (see processes 1108-1114), in-line failure analysis can be performed using an in-line failure analysis processor 152 to determine the root cause of the defect (see process 1118) and, based on the results of the in-line failure analysis, advanced process control (APC) can be performed in order to prevent the re-occurrence of the defect in subsequently manufactured IC chips (see process 1120).

More specifically, the method can further include receiving, by an image processor 151 from an optical inspection tool 131 (e.g., from a SEM), a digital 2D image (e.g., a digital 2D SEM image) of an area of a semiconductor wafer (or a fragment thereof) and converting, by the image processor 151, that digital 2D image into a virtual three-dimensional (3D) image (see process 1108).

To accomplish process 1108, the method can include determining if the 2D image is a colored 2D image or a grayscale 2D image and, if the 2D image is a colored 2D image, converting the colored 2D image into a grayscale 2D image (see process 1110). Techniques for converting a colored image into a grayscale image are well known in the art. Thus, the details of those techniques have been omitted from this specification in order to allow the reader to focus on the salient aspects of the disclosed method.

Next, the materials and topography of the surface shown in the grayscale 2D image can be determined (see process 1112).

Specifically, as discussed in detail above with regard to the system 100 and FIGS. 2A and 2B, within a grayscale 2D image (e.g., a grayscale 2D SEM image, a grayscale 2D TEM image, etc.), different shapes will have different image intensities. Furthermore, variations in these image intensities will depend upon both the different surface materials (i.e., the materials that emit the secondary electrons captured by the electron detector) and the distances between those surface materials and the electron detector. FIG. 3 is an exemplary 2D SEM image 300 showing the surface of an area of a semiconductor wafer. Visible at the surface are alternating light and dark stripes. The light stripes correspond to the tops of semiconductor fins 310 and the dark stripes correspond to the tops of isolation regions between the semiconductor fins 310. The image intensity of the semiconductor fins 310 is relatively high and is greater than the image intensity of the isolation regions 320, as indicated by the fact that the semiconductor fins 310 are light and the isolation regions 320 are dark. Ideally, the semiconductor fins 310 will have essentially identical widths and heights, will be essentially vertical (i.e., oriented essentially perpendicular to the substrate) and will have an essentially uniform pitch such that the spacing between each pair of adjacent semiconductor fins 310 is essentially identical. Also, ideally, the spaces between each pair of adjacent semiconductor fins 310 will be partially filled with dielectric fill material, thereby forming the isolation regions and the tops of the isolation regions will all be essentially level and below the tops of the semiconductor fins. However, FIG. 3 further shows a defect 350 within the area, where the distance between a pair of adjacent semiconductor fins is greater than some threshold distance and where the image intensity of the portion 320' of an isolation region between the adjacent semiconductor fins is lower than the image intensity of the isolation regions elsewhere in the area, as indicated by the fact that this portion 320' is darker than any other isolation region within the region. Due to the nature of the 2D image, as discussed above, one could look at the 2D SEM image shown in FIG. 3 and identify the defect 350, but could not determine either of the following: (a) whether the pair of adjacent semiconductor fins are vertical, but spaced to far apart, or whether one of the semiconductor fins is bent; and (b) whether the portion 320' of the isolation region is darker because it is made of a different material than the isolation regions elsewhere in the are or because its top surface is lower.

The materials of the shapes in the surface shown in the 2D image can be determined at process 1112 using a materials analysis tool 132 (e.g., an energy-dispersive X-ray image spectroscope (EDXS) or X-ray photoelectron spectroscope (XPS)) that performs a materials analysis of the surface and that generates a report identifying the different surface materials. Referring again to FIG. 3, the results of the materials analysis could, for example, indicate that the light stripes are composed of a specific semiconductor material (e.g., silicon) and the dark stripes are composed of a specific dielectric material (e.g., silicon dioxide). These results can further indicate that even though the portion 320' is darker (i.e., has a lower image intensity), it is composed of the same specific dielectric material as the isolation regions elsewhere in the area. Thus, these results indicate that the topography is uneven and, particularly, that the portion 320' is farther from the electron detector.

The topography of the surface shown in the 2D image can be determined at process 1112 based on the image intensities of the different shapes shown in the 2D image and further based on the results of the materials analysis.

Specifically, the method can include storing, in memory 110, grayscale-to-image intensity conversion information and material-specific image intensity information. For example, the method can include storing, in memory 110, multiple look-up tables (LUTs) including a grayscale LUT 113 and a material-specific image intensity LUT 114. The grayscale LUT 113 can include, for example, digital images from black to white on the grayscale and, for each digital image, an indication of the corresponding image intensity (e.g., from 0 to 100). The material-specific image intensity look-up table (LUT) 114 can list multiple different materials, which are used in integrated circuit (IC) chip manufacturing. These materials can include, for example, semiconductor materials (e.g., silicon, silicon germanium, silicon germanium carbide, polysilicon, etc.), dielectric materials (e.g., silicon dioxide, silicon nitride, silicon oxycarbide, etc.), metals, metal alloys, and any other material used in IC chip manufacturing. The material-specific image intensity LUT 114 can further associate specific image intensity information with each of the listed materials (i.e., can include material-specific image intensity information). The image intensity information can include, for example, the expected image intensity value of each material at a minimum distance ($d_{min}$) from the electron detector and also the expected image intensity values of each material at additional incrementally increasing distances from the electron detector (e.g., at $d_{min}+x$, at $d_{min}+2x$, at $d_{min}+3x$, and so on). It should be noted that this material-specific image intensity information can be empirically determined and can be specific for the given optical inspection tool being used.

This grayscale LUT 113 can be accessed and used to determine the image intensities of the different shapes shown in the grayscale 2D image given the different levels of brightness of those shapes. Then, the material-specific image intensity LUT 114 can be accessed and material-specific image intensity information can be retrieved. Given the previously determined image intensities of the different shapes shown in the grayscale 2D image and the previously determined materials of those shapes, the distances (e.g., $d_{min}$, $d_{min}+x$, at $d_{min}+2x$, at $d_{min}+3x$, etc.) between the shapes and the electron detector at the time of image capture can be determined. Once these distances are determined, they can be pieced together to determine the topography of the surface shown in the 2D image. It should be understood that the tops of shapes at distance $d_{min}$ will be at the highest level ($h_{max}$) of the topography, the tops of shapes at distance $d_{min}+x$ will be at the second highest level ($h_{max}-x$), the tops of shapes at distance $d_{min}+2x$ will be at the third highest level ($h_{max}-2x$), and so on.

Once the surface materials of the shapes and the topography of the surface are determined at process 1112, the 2D image can be converted into a virtual 3D image using a programming language (e.g., MATLAB, Python, C++, Scilab, Mathematica, Labscript or any other suitable programming language) (see process 1114). Techniques for converting 2D images into 3D images using such programming languages are well known in the art. Thus, the details of those techniques have been omitted from this specification in order to allow the reader to focus on the salient aspect of the disclosed method. See the more detailed explanation of this conversion process in the discussion of the system embodiment above. In any case, FIG. 4 is an exemplary virtual 3D image 400 generated, as described above, based on the 2D SEM image 300 shown in FIG. 3.

This virtual 3D image can subsequently be used (e.g., by an in-line failure analysis processor 152) to perform an in-line failure analysis in order to confirm the presence of the defect in the area at issue and to determine the root cause of the defect (see process 1118). For example, the defect 350 shown in the virtual 3D image 400 of FIG. 4 can be evaluated at process 1118 and a determination can be made that the outermost semiconductor fin 310' is tilted (i.e., bent) and, as a result, the space between this outermost semiconductor fin 310' and the adjacent semiconductor fin 310 is relatively wide so that the portion 320' of the isolation region between those fins only partially fills the space (i.e., the portion 320' is recessed as compared to the isolation regions elsewhere in the area).

Advanced process control (APC) can then be performed (e.g., by a processor controller 153) based on the results of the in-line failure analysis (see process 1120). That is, one or more manufacturing processes can be adjusted in order to prevent re-occurrence of the defect during subsequent integrated circuit chip manufacturing (i.e., on upcoming semiconductor wafers in the manufacturing line). For example, given the root cause of the defect shown in FIG. 4 (e.g., a titled semiconductor fin), the processes performed during semiconductor fin formation can be adjusted to prevent semiconductor fin bending. Those skilled in the art would recognize that various different processes could be adjusted alone and/or in combination to prevent such semiconductor fin bending. In one embodiment, the etch specifications used during semiconductor fin formation could be adjusted to ensure that the resulting semiconductor fins are slightly tapered (e.g., slightly wider at the bottom than at the top) and, thereby more robust.

Optionally, if, during the in-line optical inspection at process 1106, a defect is confirmed and classified as, for example, a critical defect, an off-line failure analysis can be performed (e.g., by an off-line failure analysis system 190) in order to confirm and possibly expand upon the results of the in-line failure analysis (see process 1122). The off-line failure analysis can be, for example, a non-destructive analysis, such as atomic force microscopy (AFM), and/or a destructive physical analysis (DPA). FIG. 6 is an exemplary vertical cross-section image 600 captured during an off-line failure analysis and showing the defect 350. This cross-section image 600 confirms that the outermost semiconductor fin 310' is tilted (i.e., bent) and that the portion 320' of the isolation region only partially fills the space between the pair of adjacent semiconductor fins (i.e., the portion 320' is recessed as compared to the isolation regions elsewhere in the area). Additional APC can be performed, as necessary, based on the results of the off-line failure analysis.

It should be noted that the above-described techniques, which are used to convert a 2D image into a virtual 3D image at process 1108 can, at times, produce edge effect-induced anomalies in the virtual 3D image. Specifically, a 2D SEM image may show lines, which correspond to the interfaces between two different materials and which have image intensities that are actually different from the immediately adjacent materials on either side. Depending upon the image intensities of these lines, they can appear as divots or bumps in the virtual 3D image (e.g., see FIGS. 7-8 and the detailed discussion above). Therefore, optionally, in the method, the virtual 3D image can be evaluated (e.g., by the image processor 151) before the in-line failure analysis is performed in order to determine whether it includes any edge effect-induced anomalies and, particularly, any divots or bumps caused by an edge effect (see process 1116). If so, a filter can be used by the image processor 151 to compensate for the edge effect and the virtual 3D image can be reconstructed without the anomalies (e.g., see FIGS. 9-10 and the detailed discussion above). For improved accuracy, the in-line failure analysis can be performed by the in-line failure analysis processor 152 using this reconstructed virtual 3D image.

In the above-described system and method embodiments, the in-line failure analysis can be performed significantly faster and at a reduced cost than any off-line failure analysis (which are typically time consuming and which require manpower and the performance of significant logistic and analytical processes). Thus, the disclosed system and method embodiments allow for essentially real-time advanced process control (APC) at a relatively low cost.

Also disclosed herein are embodiments of a computer program product. The computer program product can include a computer readable storage medium having program instructions embodied therewith. The program instructions can be executable by a computer to cause the computer to perform the above-described method. More particularly, the present invention may be a system, a method, and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

Figure 12:
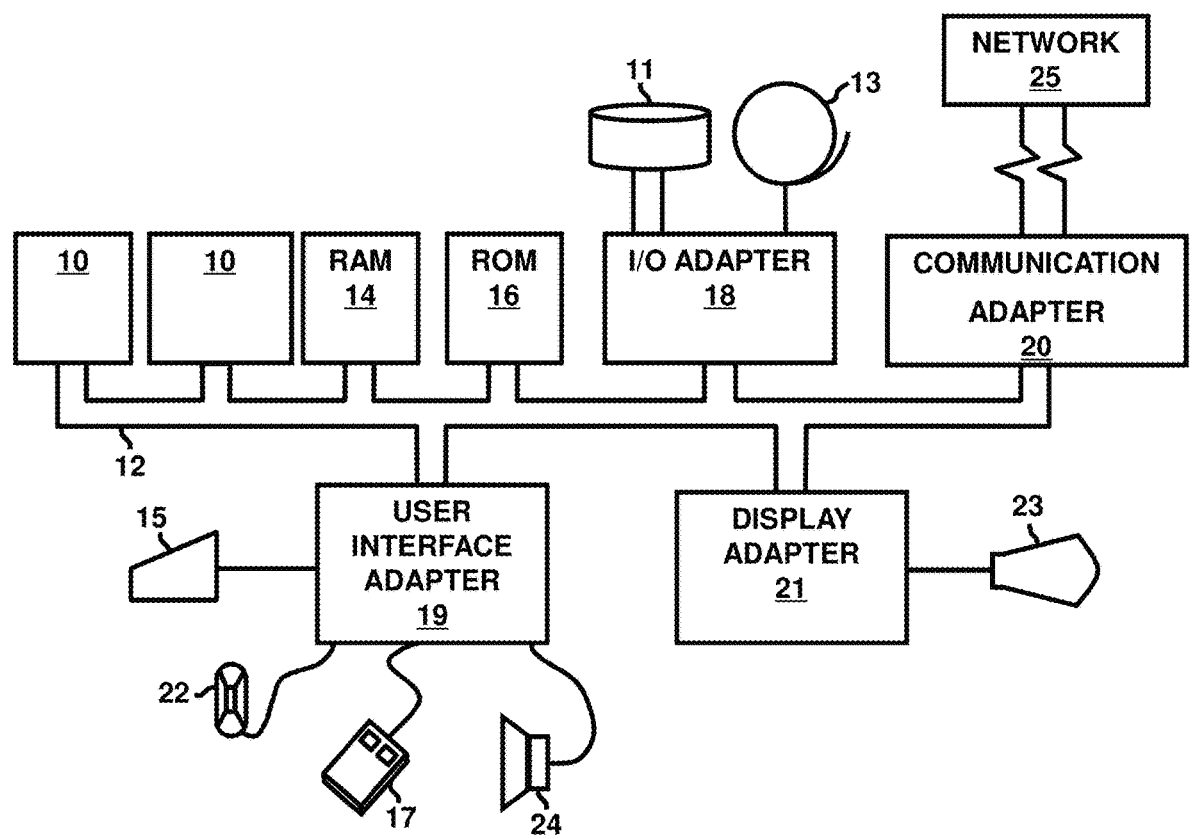
FIG. 12 is a schematic diagram illustrating an exemplary computer system that can be used to implement the system, method and computer program product embodiments disclosed herein.

FIG. 12 depicts a representative hardware environment for implementing the system, method and computer program product embodiments disclosed herein. Specifically, this schematic drawing illustrates a hardware configuration of an information handling/computer system. This computer system comprises at least one processor or central processing unit (CPU) 10. The CPUs 10 are interconnected via a system bus 12 to various devices such as a random access memory (RAM) 14, read-only memory (ROM) 16, and an input/output (I/O) adapter 18. The I/O adapter 18 can connect to peripheral devices, such as disk units 11 and tape drives 13, or other program storage devices that are readable by the system. The system can read the inventive instructions on the program storage devices and follow these instructions to execute the methodology of the embodiments herein. The system further includes a user interface adapter 19 that connects a keyboard 15, mouse 17, speaker 24, microphone 22, and/or other user interface devices such as a touch screen device (not shown) to the bus 12 to gather user input. Additionally, a communication adapter 20 connects the bus 12 to a data processing network 25, and a display adapter 21 connects the bus 12 to a display device 23 which may be embodied as an output device such as a monitor, printer, or transmitter, for example.

It should be understood that the terminology used herein is for the purpose of describing the disclosed structures and methods and is not intended to be limiting. For example, as used herein, the singular forms "a", "an" and "the" are intended to include the plural forms as well, unless the context clearly indicates otherwise. Additionally, as used herein, the terms "comprises" "comprising", "includes" and/or "including" specify the presence of stated features, integers, steps, operations, elements, and/or components, but do not preclude the presence or addition of one or more other features, integers, steps, operations, elements, components, and/or groups thereof. Furthermore, as used herein, terms such as "right", "left", "vertical", "horizontal", "top", "bottom", "upper", "lower", "under", "below", "underlying", "over", "overlying", "parallel", "perpendicular", etc., are intended to describe relative locations as they are oriented and illustrated in the drawings (unless otherwise indicated) and terms such as "touching", "in direct contact", "abutting", "directly adjacent to", "immediately adjacent to", etc., are intended to indicate that at least one element physically contacts another element (without other elements separating the described elements). The term "laterally" is used herein to describe the relative locations of elements and, more particularly, to indicate that an element is positioned to the side of another element as opposed to above or below the other element, as those elements are oriented and illustrated in the drawings. For example, an element that is positioned laterally adjacent to another element will be beside the other element, an element that is positioned laterally immediately adjacent to another element will be directly beside the other element, and an element that laterally surrounds another element will be adjacent to and border the outer sidewalls of the other element. The corresponding structures, materials, acts, and equivalents of all means or step plus function elements in the claims below are intended to include any structure, material, or act for performing the function in combination with other claimed elements as specifically claimed.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

What is claimed is:

1. A system comprising:
 a memory storing material-specific image intensity information, the material-specific image intensity information comprising expected image intensity values of multiple different materials at multiple different distances from a detector of an optical inspection tool; and
 an image processor performing the following:
  receiving, from the optical inspection tool, a two-dimensional image of a surface of an area of a semiconductor wafer, the two-dimensional image being captured by the optical inspection tool during manufacturing of integrated circuit chips on the semiconductor wafer and the two-dimensional image showing different shapes with different image intensities;

accessing the material-specific image intensity information from the memory; and converting the two-dimensional image into a virtual three-dimensional image using the different image intensities of the different shapes in the two-dimensional image and further using the material-specific image intensity information, wherein the virtual three-dimensional image is usable for performing an in-line failure analysis to determine a root cause of a defect.

2. The system of claim 1, wherein the optical inspection tool comprises a scanning electron microscope, the detector comprises an electron detector, the two-dimensional image being a grayscale image and the image intensity values being indicative of relative brightness from black to white.

3. The system of claim 1,
the image processor further performing the following prior to the converting:
determining the different image intensities of the different shapes in the two-dimensional image;
determining different materials of the different shapes;
retrieving, from the memory, image intensity information for each of the different materials; and
determining a topography of the surface based on the image intensity information for each of the different materials,
wherein the two-dimensional image is converted into the virtual three-dimensional image given the topography.

4. The system of claim 3, further comprising a materials analysis tool that performs a materials analysis of the surface, wherein the image processor further receives, from the materials analysis tool, results indicating the different materials of the different shapes.

5. The system of claim 4, wherein the materials analysis tool comprises an energy-dispersive X-ray spectroscope.

6. The system of claim 1,
wherein the image processor further performs the following before the in-line failure analysis is performed:
determines whether the virtual three-dimensional image includes an anomaly caused by an edge effect;
uses a filter to compensate for the edge effect; and
after the using of the filter, reconstructs the virtual three-dimensional image.

7. The system of claim 1, wherein the image processor converts the two-dimensional image into the virtual three-dimensional image using a programming language.

8. The system of claim 1, further comprising:
an in-line failure analysis processor in communication with the image processor, wherein the in-line failure analysis processor uses the virtual three-dimensional image to perform the in-line failure analysis; and
a process controller in communication with the in-line failure analysis processor performing advanced process control based on results of the in-line failure analysis.

9. The system of claim 8, further comprising performing, by an off-line failure analysis system, an off-line failure analysis to confirm the results of the in-line failure analysis.

10. A method comprising:
receiving, by an image processor from an optical inspection tool, a two-dimensional image of a surface of an area of a semiconductor wafer, the two-dimensional image being captured by the optical inspection tool during manufacturing of integrated circuit chips on the semiconductor wafer and the two-dimensional image showing different shapes with different image intensities;

accessing, by the image processor from a memory, material-specific image intensity information stored in the memory, the material-specific image intensity information comprising expected image intensity values of multiple different materials at multiple different distances from a detector of the optical inspection tool; and converting, by the image processor, the two-dimensional image into a virtual three-dimensional image using the different image intensities of the different shapes in the two-dimensional image and further using the material-specific image intensity information, wherein the virtual three-dimensional image is usable for performing an in-line failure analysis to determine a root cause of a defect.

11. The method of claim 10, wherein the optical inspection tool comprises a scanning electron microscope, the detector comprises an electron detector, the two-dimensional image being a grayscale image and the image intensity values being indicative of relative brightness from black to white.

12. The method of claim 10, further comprising performing the following after the receiving of the two-dimensional image and prior to the converting of the two-dimensional image into a virtual three-dimensional image:
determining the different image intensities of the different shapes in the two-dimensional image;
determining different materials of the different shapes;
retrieving, from the memory, image intensity information for each of the different materials; and
determining a topography of the surface based on the image intensity information for each of the different materials,
wherein the two-dimensional image is converted into the virtual three-dimensional image given the topography.

13. The method of claim 10, further comprising: receiving, by the image processor from a materials analysis tool, results of a materials analysis indicating the different materials of the different shapes.

14. The method of claim 13, wherein the materials analysis tool comprises an energy-dispersive X-ray spectroscope.

15. The method of claim 10, further comprising:
determining, by the image processor, whether the virtual three-dimensional image includes an anomaly caused by an edge effect;
using, by the image processor, a filter to compensate for the edge effect; and
after the using of the filter, reconstructing the virtual three-dimensional image.

16. The method of claim 10, wherein the image processor converts the two-dimensional image to the virtual three-dimensional image using a programming language.

17. The method of claim 11, further comprising:
using, by an in-line failure analysis processor in communication with the image processor, the virtual three-dimensional image to perform the in-line failure analysis; and
performing, by a process controller, advanced process control based on results of the in-line failure analysis.

18. The method of claim 17, further comprising, performing, by an off-line failure analysis system, an off-line failure analysis to confirm the results of the in-line failure analysis.

19. A computer program product comprising a non-transitory computer readable storage medium having program instructions embodied therewith, the program instructions being executable by a computer to cause the computer to perform a method, the method comprising:

receiving, from an optical inspection tool, a two-dimensional image of a surface of an area of a semiconductor wafer, the two-dimensional image being captured by the optical inspection tool during manufacturing of integrated circuit chips on the semiconductor wafer and the two-dimensional image showing different shapes with different image intensities;

accessing material-specific image intensity information stored in memory, the material-specific image intensity information comprising expected image intensity values of multiple different materials at multiple different distances from a detector of an optical inspection tool; and converting the two-dimensional image into a virtual three-dimensional image using the different image intensities of the different shapes in the two-dimensional image and further using the material-specific image intensity information, wherein the virtual three-dimensional image is usable for determining a root cause of a defect in the area.

20. The computer program product of claim 19, wherein the method further comprises performing the following after the receiving of the two-dimensional image and prior to the converting of the two-dimensional image into the virtual three-dimensional image:

determining the different image intensities of the different shapes in the two-dimensional image;

determining different materials of the different shapes;

retrieving, from the memory, image intensity information for each of the different materials; and determining a topography of the surface based on the image intensity information for each of the different materials, wherein the two-dimensional image is converted into the virtual three-dimensional image given the topography.

* * * * *